(12) United States Patent
Fleige et al.

(10) Patent No.: US 11,253,599 B2
(45) Date of Patent: Feb. 22, 2022

(54) ANALGESIC PREPARATION WITH NANOCARRIERS AND USE THEREOF

(71) Applicant: DendroPharm GmbH, Berlin (DE)

(72) Inventors: Emanuel Fleige, Berlin (DE); Sam Moré, Dresden (DE); Michael Unbehauen, Berlin (DE); Rainer Haag, Berlin (DE); Christoph Stein, Berlin (DE); Halina Machelska-Stein, Berlin (DE); Florian Paulus, Munich (DE)

(73) Assignee: DendroPharm GmbH, Berlin (DE)

(*) Notice: Subject to any disclaimer, the term of this patent is extended or adjusted under 35 U.S.C. 154(b) by 0 days.

(21) Appl. No.: 15/780,954

(22) PCT Filed: Dec. 8, 2016

(86) PCT No.: PCT/DE2016/100569
§ 371 (c)(1),
(2) Date: Jun. 1, 2018

(87) PCT Pub. No.: WO2017/097291
PCT Pub. Date: Jun. 15, 2017

(65) Prior Publication Data
US 2018/0344857 A1 Dec. 6, 2018

(30) Foreign Application Priority Data
Dec. 8, 2015 (DE) .................. 102015121366.4

(51) Int. Cl.
*A61K 47/34* (2017.01)
*A61K 31/485* (2006.01)
(Continued)

(52) U.S. Cl.
CPC .......... *A61K 47/34* (2013.01); *A61K 9/5146* (2013.01); *A61K 9/5153* (2013.01);
(Continued)

(58) Field of Classification Search
CPC ...... A61K 47/34; A61K 9/5146; A61K 47/10; A61K 9/5153; A61K 31/485; A61K 31/40;
(Continued)

(56) References Cited

U.S. PATENT DOCUMENTS

2010/0081773 A1* 4/2010 Multhaup ............ A61K 9/5146
525/450
2010/0284960 A1* 11/2010 Riggs-Sauthier .... A61K 9/4858
424/78.36

FOREIGN PATENT DOCUMENTS

DE 102014008575 A1 12/2015
WO 2006018295 A2 2/2006
(Continued)

OTHER PUBLICATIONS

Haag et al. (WO 2006018295 A2 English translation) (Year: 2006).*
(Continued)

*Primary Examiner* — Quanglong N Truong
(74) *Attorney, Agent, or Firm* — Thomas|Horstemeyer LLP (57) ABSTRACT

The invention relates to the field of analgesics. According to the invention, a kit or composition, particularly a pharmaceutical composition or a pharmaceutical kit, is provided, comprising a nanocarrier which is a hyperbranched polymer, such as a dendritic polymer or dendrimer, preferably having a molecular weight of 1,000-100,000 g/mol, and an analgesic which, when administered without nanocarrier, has both peripheral and central analgesic effect, preferably an opioid such as nalbuphine. According to the invention, the analgesic in this composition mainly or exclusively has a peripheral effect and thus reduces side effects triggered by the activation of central or intestinal opioid receptors. It is used for the treatment of peripheral pain and/or inflammation.

(Continued)

a)

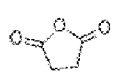 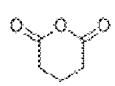 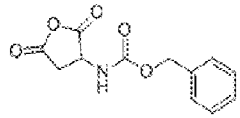

succinic anhydride  glutaric anhydride  N-Cbz-L-aspartic anhydride b) c)

The invention also relates to particularly suitable nanocarriers.

15 Claims, 4 Drawing Sheets

(51) Int. Cl.
| | |
|---|---|
| *A61K 31/40* | (2006.01) |
| *A61K 9/51* | (2006.01) |
| *A61P 25/04* | (2006.01) |
| *A61K 47/10* | (2017.01) |
| *A61K 31/135* | (2006.01) |
| *A61K 31/44* | (2006.01) |

(52) U.S. Cl.
CPC ............ *A61K 9/5192* (2013.01); *A61K 31/40* (2013.01); *A61K 31/485* (2013.01); *A61K 47/10* (2013.01); *A61P 25/04* (2018.01); *A61K 31/135* (2013.01); *A61K 31/44* (2013.01); *A61K 2300/00* (2013.01)

(58) Field of Classification Search
CPC .............. A61K 9/5192; A61K 2300/00; A61K 31/135; A61P 25/04
See application file for complete search history.

(56) References Cited

FOREIGN PATENT DOCUMENTS

| | | |
|---|---|---|
| WO | 2009123934 A2 | 10/2009 |
| WO | 2011011384 A2 | 1/2011 |

OTHER PUBLICATIONS

International Search Report issued by the European Patent Office for application PCT/DE2016/100569, dated Apr. 5, 2017.
Ward et al., Sustained Analgesia Achieved Through Esterase-Activated Morphine Prodrugs Complexed with PAMAM Dendrimer, Pharmaceutical Research, p. 247-256, 2012.
Carrasco-Sanchez et al., In situandin silicoevaluation of amine- and folate-terminated dendrimers as nanocarriers of anesthetics, European Journal of Medicinal Chemistry, p. 250-257, 2013.
Calderon et al., Dendritic Polyglycerols for Biomedical Applications, Advanced Materials, p. 190-218, 2009.
Baker et al., Pre-Clinical Considerations in the Assessment of Immunogenicity for Protein Therapeutics, Current Drug Safety, 5, 308-313, 2010.
Brown et al., The Use of Quaternary Narcotic Antagonists in Opiate Research, Neuropharmacology, vol. 24, No. 3, 181-191, 1984.
Bunczsak-Reeh et al., Effect of Inflammation on the Delivery of Drugs to Dental Pulp, Journal of Endodontics 24, 822-825, 1998.
Cheng et al., Multifunctional Nanoparticles: Cost Versus Benefit of Adding Targeting and Imaging Capabilities, Science 338, 903-910, 2012.
Fleige et al., Aggregation Phenomena of Host and Guest upon the Loading of Dendritic Core-Multishell Nanoparticles with Solvatochramie Dyes, Macromolecules 45, 9452-9459, 2012.
Fleige et al., Dendronized core-multishell nanocarriers for solubilization of guest molecules, Nanocarriers vol. 1, 1-9, 2013.
Guthrie et al., Characterization of a sterile soft-tissue inflammation model in Thoroughbred horses, J. vet. Pharmacol. Therap. 19, 44-49, 1996.
Haag et al., An Approach to Core-Shell-Type Architectures in Hyperbranched Polyglycerols by Selective Chemical Differentiation, Macromolecules 33, 8158-8166, 2000.
Haag et al., Dendritic Aliphatic Polyethers as High-Loading Soluble Supports for Carbonyl Compounds and Parallel Membrane Separation Techniques, J. Comb. Chem. 4, 112-119, 2002.
Hawker et al., One-Step Synthesis of Hyperbranched Dendritic Polyesters, J. Am. Chem. Soc. 113, 4583-4588, 1991.
Hua et al., Targeted Nanoparticles that Mimic Immune Cells in Pain Control Inducing Analgesic and Anti-inflammatory Actions: A Potential Novel Treatment of Acute and Chronic Pain Conditions, Pain Physician 16, E199-216, 2013.
Kalso et al., No pain, No gain: clinical excellence and scientific rigour—lessons learned from IA morphine, Pain 98, 269-275, 2002.
Koshkaryev et al., Immunoconjugates and long circulating systems: Origins, current state of the art and future directions, Adv Drug Deliv Rev 65, 24-35, 2013.
Baigent, Vascular and upper gastrointestinal effects of non-steroidal anti-infl ammatory drugs: meta-analyses of individual participant data from randomised trials, Lancet 382:769-79, 2013.
Moshourab et al., Fentanyl decreases discharges of C and A nociceptors to suprathreshold mechanical stimulation in chronic inflammation, J Neurophysiol 108:2827-2836, 2012.
Nockemann et al., The K+ channel GIRK2 is both necessary and sufficient for peripheral opioid-mediated analgesia, EMBO Mol Med 5, 1263-1277, 2013.
Ovadia et al., Improvement of drug-like properties of peptides: the somatostatin paradigm, Expert Opin Drug Discov 5, 655-671, 2010.
Paulozzi, Prescription drug overdoses: A review, Journal of Safety Research 43,283-289. 2012.
Radowski et al., Supramolecular Aggregates of Dendritic Multishell Architectures as Universal Nanocarriers, Angew Chem Int Ed Engl 46, 1265-1269, 2007.
Schumacher et al., Opioid Analgesics & Antagonists, Basic and Clinical Pharmacology, 531-558, 2009.
Steen et al., Inflammatory mediators potentate pain induced by experimental tissue acidosis, Pain 66, 163-170, 1996.
Stein et al., Unilateral Inflammation of the Hindpaw in Rats as a Model of Prolonged Noxious Stimulation:Alterations in Behavior and Nociceptive Thresholds, Pharmacol Biochem Behav 31, 445-451, 1998.
Stein et al., Opioids from immunocytes interact with receptors on sensory nerves to inhibit nociception in inflammation, Proc. Natl. Acad. Sci. vol. 87, 5935-5939, 1990.
Stein et al., Analgesic Effect of Intraarticular Morphine After Arthroscopic Knee Surgery, N Engl J Med 325, 1123-1126, 1991.
Stein, Peripheral Mechanisms of Opioid Analgesia, Anesth Analg 76, 182-191, 1993.
Epstein, The Control of Pain in Peripheral Tissue by Opioids, Mechanishm of Disease vol. 332, No. 25, 1685-90, 1995.
Stein et al., Attacking pain at its source: new perspectives on opioids, Nat Med 9, 1003-1008, 2003.
Stein et al., Peripheral Mechanisms of Pain and Analgesia, Brain Res Rev 60,90-113, 2009.
Stein et al., Modulation of Peripheral Sensory Neurons by the Immune System: Implications for Pain Therapy, Pharmacol Rev 63, 860-881, 2011.
Stein et al., Targeting inflammation and wound healing by opioids, Trends Pharmacol Sci 34, 303-312, 2013.
Sunder et al., Controlled Synthesis of Hyperbranched Polyglycerols by Ring-Opening Multibranching Polymerization, Macromolecules, 32, 4240-4246, 1999.
Sunder et al., Controlling the Growth of Polymer Trees: Concepts and Perspectives For Hyperbranched Polymers, Chemistry 6, 2499-2506, 2000.
Tabas et al., Anti-Inflammatory Therapy in Chronic Disease: Challenges and OpportunitiesScience 339, 166-172, 2013.
Tulamo, Sequential clinical and synovial fluid changes associated with acute infectious arthritis in the horse, Equine Vet J 21, 325-331, 1989.
Vadivelu et al., Peripheral opioid receptor agonists for analgesia: A comprehensive review, J Opioid Manag 7, 55-68, 2011.
Woo et al., Changes in Tissue pH and Temperature after Incisio Indicate Acidosis May Contribute to Postoperative Pain, Anesthesiology 101, 468-475, 2004.
Zöllner et al., Opioids, Handb Exp Pharmacol, 31-63, 2007.

\* cited by examiner

Fig. 1 a)

succinic anhydride  glutaric anhydride  N-Cbz-L-aspartic anhydride b)

ANALGESIC PREPARATION WITH NANOCARRIERS AND USE THEREOF

The invention relates to the field of analgesics. A kit or composition, in particular a pharmaceutical composition or a pharmaceutical kit, is provided, which comprises a nanocarrier, preferably having a molecular weight of 1,000-100,000 g/mol, and an analgesic, which, when administered without nanocarrier, has analgesic action in both the peripheral and the central nervous system (CNS), and which is preferably an opioid. According to the invention, in this composition, the analgesic mainly or exclusively has peripheral action, and thus reduces side effects which are triggered by the activation of central or intestinal opioid receptors. It is used to treat peripheral pain and/or inflammation. The invention also relates to particularly suitable nanocarriers.

The activation of opioid receptors in injured or inflamed peripheral tissue can reduce pain. Activation of opioid receptors in the intestinal or central nervous system (central action), however, causes side effects such as constipation, sedation, apnea or addiction. This limits the utility of conventional opioids for pain relief. Formulations of opioid agonists for systemic administration that are substantially peripherally effective are so far not available for patient treatment.

Conventional opioid receptor agonists such as e.g. morphine are the gold standard for the treatment of severe pain. However, their use is associated with side effects, which essentially result in permeation of the blood-brain barrier (BBB) and finally activation of opioid receptors in the CNS. The consequences are among others sedation, apnea, tolerance, dependency, abuse or overdose with fatal consequences [Schumacher, M. A. et al., Basic and clinical pharmacology (eds. Katzung, B. G., Masters, S. B. & Trevor, A. J.) 531-552 (McGraw-Hill Medical, New York, 2009), Paulozzi, L. J. et al., J Safety Res 43, 283-289 (2012)]. Activation of intestinal opioid receptors in the non-inflamed (intact) gastrointestinal tract may also induce constipation. Non-steroidal anti-inflammatory drugs are alternatives, but they also cause harmful side effects such as gastrointestinal bleeding, ulcers, or cardiovascular complications (Lancet 382: 769-79, 2013). New painkillers are therefore urgently needed.

Conventional stronger mu-opioid receptor agonists such as e.g. morphine or oxycodone have a significant potential for abuse and addiction due to their euphoric effect. The current state of the art therefore is a combination with a partial kappa opioid receptor agonist or an antagonist such as naloxone. Examples are oxycodone/naloxone combination products. Oxycodone (ATC N02AA55) is a semi-synthetic opioid with analgesic properties. Naloxone is a competitive antagonist on all opioid receptors, which in the dosage used here locally cancels the effect of oxycodone in the intestine, and thus is added to prevent the emergence of constipation. Nevertheless, about 50% of all patients treated with oxycodone/naloxone combinations still need supportive laxative therapy to prevent severe constipation. At higher doses, euphoric (addictive) effects mediated by central mu-opioid receptors can also not be completely prevented with this combination.

An alternative to mu-opioid receptor agonists might be kappa opioid receptor agonists. First results with so-called kappa agonists in the 1980s initially brought this goal within reach, however, it soon became clear that these substances—when overcoming the BBB—not only caused an aversion to the drug, but also hallucinations, sedation and depression-like symptoms. Due to these pronounced side effects, there are only a few analgesics such as butorphanol and buprenorphine based on at least partial kappa opioid receptor agonist activity. Although the pronounced dysphoric and hallucinogenic effects of kappa agonists in particular prevent formation of addiction and drug abuse, they also constitute one of the main obstacles to analgesic use.

Micellar nanocarrier opioid formulations have already been developed, such as liposomal morphine. The main characteristic of these formulations is a retardation of the duration of action and the increase in the solubility of the active ingredient. Liposomal carriers and nanocarriers of amphiphilic micelles are generally known to increase drug transmission across the BBB.

However, opioid receptors are not only localized in the brain, but are also formed in peripheral sensory neurons and can block their excitation by painful stimuli [Stein, C. et al., Proc Natl Acad Sci USA 87, 5935-5939 (1990); Moshourab, R. et al., J Neurophysiol 108, 2827-2836 (2012); Nockemann, D. et al., EMBO Mol Med 5, 1263-1277 (2013); Stein, C. et al., Pharmacol Rev 63, 860-881 (2011)]. These receptors are up-regulated in peripheral, injured tissue and can be selectively targeted with opioid agonists to avoid central or intestinal side effects [Stein, C. et al., Pharmacol Rev 63, 860-881 (2011); Kalso, E. et al., Pain 98, 269-275 (2002); Vadivelu, N. et al., J Opioid Manag 7, 55-68 (2011); Stein, C. et al., N Engl J Med 325, 1123-1126 (1991); Stein, C. et al., Trends Pharmacol Sci 34, 303-312 (2013); Stein, C. et al., Nat Med 9, 1003-1008 (2003); Stein C. N Engl J Med., 332, 1685-90 (1995)]. In fact, it has already been shown, in the animal model, that pain and inflammation as well as, in humans, postoperative and arthritic pain can be efficiently reduced by local administration of low, systemically inactive doses of opioid agonists [Kalso, E. et al., Pain 98, 269-275 (2002); Stein, C. et al., Pharmacol Rev 63, 860-881 (2011)]. However, formulations of selective peripherally active opioid agonists for systemic (eg, intravenous) administration are not generally available. Previous strategies used polar opioid ligands to reduce BBB permeability, or e.g. antibody conjugates for the targeted tissue-specific release of drugs [Stein, C. Anesth Analg 76, 182-191 (1993); Hua, S. et al., Pain Physician 16, E199-216 (2013); Cheng, Z. et al., Science 338, 903-910 (2012)]. However, the use of polar opioid ligands has been largely unsuccessful because polar residues reduce the affinity of the ligands to opioid receptors, and there was no complete impermeability of the BBB at higher doses of ligands [Stein, C. et al., Pharmacol Rev 63, 860-881 (2011); Brown, D. R. et al., Neuropharmacology 24, 181-191 (1985)]. Antibody conjugates have problems such as allergic reactions, low drug loading, cross-reactivity with healthy or off-target tissue, impaired release of active agents, rapid elimination or high molecular complexity [Baker, M. et al., Curr Drug Saf 5, 308-313 (2010); Ovadia, O. et al., Expert Opin Drug Discov 5, 655-671 (2010); Koshkaryev, A. et al., Adv Drug Deliv Rev 65, 24-35 (2013); Cheng, Z. et al., Science 338, 903-910 (2012)].

In contrast to this, the inventors have set themselves the task of providing an improved composition which, with little or no central side effects, has an analgesic effect, whereby the stated problems are reduced or avoided. This problem is solved by the invention, in particular by the subject matter of the claims.

The invention provides a composition comprising
a nanocarrier having a molecular weight of 1,000-100,000 g/mol, preferably 5,000-75,000 g/mol or 8,000-50,000 g/mol, more preferably 30,000-40,000 g/mol, and
an analgesic which, when administered without nanocarrier, has both peripheral and central analgesic effects. In the context of the invention, the analgesic preferably is an opioid, e.g., a kappa receptor agonist such as nalbuphine.

In one embodiment of the invention, analgesic and nanocarrier are not covalently associated with each other. It is possible, on the one hand, for the analgesic and nanocarrier to be associated with one another via noncovalent binding, where the noncovalent binding comprises ionic interactions (for example between charged residues such as $COO^-$ or $NH_3^+$), van der Waals interactions and/or interactions of aromatic pi-electrons. In particular, nanocarriers with a core-shell structure (with one shell, one double shell or several shells) are well suited for this purpose, since such nanocarriers can be loaded with hydrophilic or hydrophobic guest molecules, in the case of the present invention, analgesics, in particular opioids.

On the other hand, it is also possible that nanocarrier and analgesic are only mixed together, so that a close association does not exists. The invention therefore also provides a kit comprising:
- a nanocarrier, e.g. having a molecular weight of 1,000-100,000 g/mol, preferably 5,000-75,000 g/mol or 8,000-50,000 g/mol, more preferably 30,000-40,000 g/mol, and
- an analgesic which, when administered without nanocarrier, has both peripheral and central analgesic effects. In the context of the invention, the analgesic preferably is an opioid, e.g. a kappa receptor agonist such as nalbuphine.

The kit according to the invention can on the one hand serve as an intermediate for a composition according to the invention which comprises the analgesic and the nanocarrier—covalently or, preferably, noncovalently, associated. On the other hand, the two constituents of the kit can also be administered separately, in which case an essentially simultaneous administration according to the invention reduces the central side effects in the best way. In this case, the nanocarrier or the analgesic can be administered first, wherein the administration is preferably carried out at intervals of 0-10 min, 0-5 min or 1-2 min. Preferably, both components are administered by the same route, e.g. both intravenous, but a different application form is also possible.

In another embodiment, the analgesic and the nanocarrier are within a composition and are covalently associated with each other. This can happen e.g. via esterification of carboxyl groups of the nanocarrier with hydroxyl groups of the analgesic, preferably of the opioid.

Within the context of the invention, the diameter of the nanocarrier can be about 3-25 nm, preferably about 5-20 nm, most preferably 10-18 nm.

Nanocarriers of the invention may be hydrophilic. Preferably, they carry charged functional groups, particularly preferably negatively charged functional groups.

In the context of the invention, the nanocarrier can be selected from the group of:
a) highly branched polymers, preferably dendritic polymers or dendrimers;
b) polydextrin-based nanocarriers; and
c) block copolymers or block copolymers based nanocarriers The nanocarriers according to the invention are preferably those from the first of these groups, i.e. unimolecular nanocarriers. Dendrimers are chemical compounds whose structure is perfectly branched from a branching core like a tree. This is called dendrimer, if these branches consist of repetitive units, thus giving a radial symmetry. These must therefore—if one starts from a core—contain branches, otherwise one would receive a chain. There can be a branching into two or more links.

It is easier to produce dendritic or highly branched polymers (hyperbranched polymers), with very similar properties, in which not all possible branching sites are branched. In the context of the invention, the nanocarriers are preferably a highly branched polyglycerol (hPG) or a highly branched polyester, which includes derivatives thereof. These highly branched polyglycerols or polyesters have a degree of branching of 25% or more, preferably 25-66% or 45-66%. Highly branched polymers differ from star polymers with a relatively low degree of branching. A star polymer has a multifunctional center which is linked to linear polymer chains of equal or different lengths and has a degree of branching of less than 25%. The degree of branching is calculated according to Hawker et al. (J. Am. Chem. Soc. 1991, 113, 4583-4588).

Such hyperbranched dendritic polyglycerol polymers or polyester polymers may e.g. be core-shell nanocarriers or core-multi-shell nanocarriers, e.g. with a double shell. In this context, layers of the nanocarrier which differ in their hydrophilicity or hydrophobicity are referred to as core or shell. For example, the core may be hydrophobic and the shell hydrophilic. One possible construction for a core multi-shell nanocarrier is, e.g., core-ester bond-diacid-ester bond-mPEG.

The nanocarriers used in the invention are hydrophilic. This may be due to the presence of polar, that is to say hydrophilic and/or charged groups, e.g. hydroxyl groups, carboxyl groups, amino groups, sulfate groups or succinate groups. They may be anionic or cationic functional groups. The functional groups may be biodegradable. In the nanocarriers of the invention, preferably, 2-50%, more preferably 5-15%, of the functional terminal groups are functionalized with ionic groups, preferably with negative charge. These groups can also be inside the nanocarrier.

In one embodiment of the invention, the composition according to the invention does not comprise the compounds described in DE 102014008575.9, i.e., it does not comprise a conjugate of a hydrophilic polymer such as polyglycerol with biodegradable anionic end groups such as succinate, linked, e.g., via an ester group, with an analgesic agent such as morphine or another opioid receptor ligand. In another embodiment, corresponding conjugates are used according to the invention.

In a preferred embodiment, the nanocarrier is a unimolecular nanocarrier with dendritic structure, wherein the nanocarrier preferably consists of a dendritic core and at least two shells, wherein an inner shell is connected through a first linker with the dendritic core and an outer shell is connected to the inner shell through a second linker. In one embodiment, the nanocarriers are neutral, cationic or anionic; preferably, they are charged. Corresponding nanocarriers are disclosed, e.g., in WO 2006/018295 A2. Nanocarriers, as disclosed in Radowski et al. (Angew. Chem. Int. Ed. 2007, 46, 1265-1269); Fleige et al. (Macromolecules 2012, 45, 9452-9459), Fleige et al. (Nanocarriers, Vol. 1, 2013, 1-9, WO2011/095311), or Haag et al., (Macromolecules, 2000, 33, 8158-8166) can also be used within the context of the invention. A unimolecular sulfated polyanionic nanocarrier, in particular a unimolecular polyanionic polyglycerol polymer having a hydrophilic shell and a hydrophobic core (EP Application No. 14 161 579.9) can also be used. Nanocarriers, which, like those nanocarriers, preferentially accumulate in inflamed areas after systemic administration are well-suited for use in the context of the present invention.

The nanocarrier can be designed so that
a) the dendritic core of the nanocarrier is made from polyglycerol, preferably having a molecular weight of 3-20 kDa, more preferably 7-10 or 8-9 kDa; and/or
b) the inner shell of the nanocarrier is a preferably linear alkyl chain having a carbon length of from C2 to C40, preferably C8-C18 or C12-C15, e.g., C15; and/or
c) the outer shell is polyethylene glycol having the structural formula ($-CH_2-CH_2O-$)$_n$ wherein n=3-130, which terminally bears a methoxy group, a hydroxyl group or a carboxyl group, preferably a methoxy group; and/or
d) the first linker between the core and the inner shell is an ester or amide bond; and/or
e) the second linker between inner and outer shell is an ester bond,
wherein, preferably, all features a-e apply.

The nanocarrier may comprise dendritic polyglycerol dodecanoic acid polyethylene glycolate. As an example, it can be characterized as follows:

Nomenclature formula: $hPG_{10000}(-NH_2)_{0.7}(C_{12}mPEG_{350})_{1.0}$ (Mn=350)

Alternative nomenclature: $hPG_{10000}(-NH_2)_{0.7}(C_{12}mPEG_6)_{1.0}$ (6 Repeating units on average)

hPG10k has about 135 functional groups, of which about 40-80%, e.g. about 70% can be converted to amines (index number 0.7).

which are covalently bound to nanocarrier do not have this disadvantage, but, due to the high synthesis cost, they are mainly economically feasible for high-priced niche applications.

A non-covalent attachment of the analgesic, particularly the opioid, is in particular possible with hPG-based nanocarriers functionalized with molecules having specific interaction points for opioids, particularly of ionic or hydrophobic nature, or the combinations thereof.

In one embodiment of the invention, positively charged drugs, e.g. opioids such as nalbuphine, are non-covalently encapsulated within the highly branched nanocarriers of the invention. A modulation of the charge of the nanocarriers may allow for a modulation of the kinetics of drug release. Preferably, the active ingredient is non-covalently encapsulated, while the nanocarrier is, e.g., at the core or via a linker, equipped with an amino-containing compound, and which is, e.g., at a suitable pH, uncharged or negatively charged to allow for high encapsulation efficiency. Suitable nanocarriers are described herein.

The charge of the nanocarrier can be modified at a different pH. To this end, the nanocarrier is chosen so that after administration of the composition, in the inflamed tissue, consequently at an acidic pH, the nanocarrier exhibits a positive charge. This accelerates the release of the likewise positively charged active substance.

Alternatively, it is also possible to delay the release of a positively charged drug by utilizing nanocarriers which are negatively charged in the target tissue having an acidic pH,

| Molecular building blocks from inside to outside | Chemical constituent Size | Synthesis module |
|---|---|---|
| 1. Dendritic core | hyperbranched poly glycerol = hPG $M_n$ = 8000-10000 Da | hyperbranched Polyglycerolamin = hPG($-NH_2$) ($M_n$ = 10 kDa, 40-80% amination, especially, 65-70%) |
| | Peptide bond | |
| 2. Lipophilic nonpolar layer of saturated fatty acids | $C_{10}$ or $C_{12}$-fatty acid chain, especially, $C_{12}$ or $C_{15}$ | C10-Diacid: 1,10-Decanedicarboxylic acid $C_{12}$-Diacid: 1,12-dodecanedicarboxylic acid $C_{15}$ Diacid: 1,15-pentadecanedicarboxylic acid |
| | Ester bond | |
| 3. Hydrophilic polyethylene glycol chain | mPEG = methoxy polyethylene glycol; $M_n$ = 350 | mPEG = methoxy polyethylene glycol; $M_n$ = 350, 500, 700 or 1000, especially 350 |

The nanocarrier can aggregate and in this aggregation take up guest molecules, in the present invention, the analgesic. Unimers and aggregates are in equilibrium, which shifts towards unimer with increasing dilution, but with slow kinetics. In addition, especially depending on the polarity and pH of the environment, a release of the guest molecules from the aggregates occurs. An advantage of the compounds described in the patent is that the viscosity of compositions made therewith is lower than for polymers with linear chains or for less branched star polymers.

In contrast to micellar encapsulated drugs, dendritic nanocarriers exhibit increased shear stability and significantly lower burst release. The latter describes the mechanism of uncontrolled spontaneous drug release upon a media change e.g. after the injection. Active pharmaceutical ingredients allowing for the preparation of sustained release compositions. In the case of a negatively charged active substance, reverse charges of the nanocarrier must be selected accordingly.

In addition, a co-encapsulation with hydrophobic ionic compounds, e.g. compounds bearing long-chain amino groups, is possible. Then, a nanocarrier can be chosen that is also neutral in inflamed tissue. The encapsulated hydrophobic ionic compounds are chosen so that they are charged in inflamed tissue, and that they modulate the kinetics of drug release, e.g., these compounds are then positively charged and accelerate the release of a positively charged drug, e.g., an opioid such as nalbuphine.

The strength of the interactions between nanocarrier and analgesic can be precisely tuned by varying the number and type of groups interacting with the drug.

Figure 1:
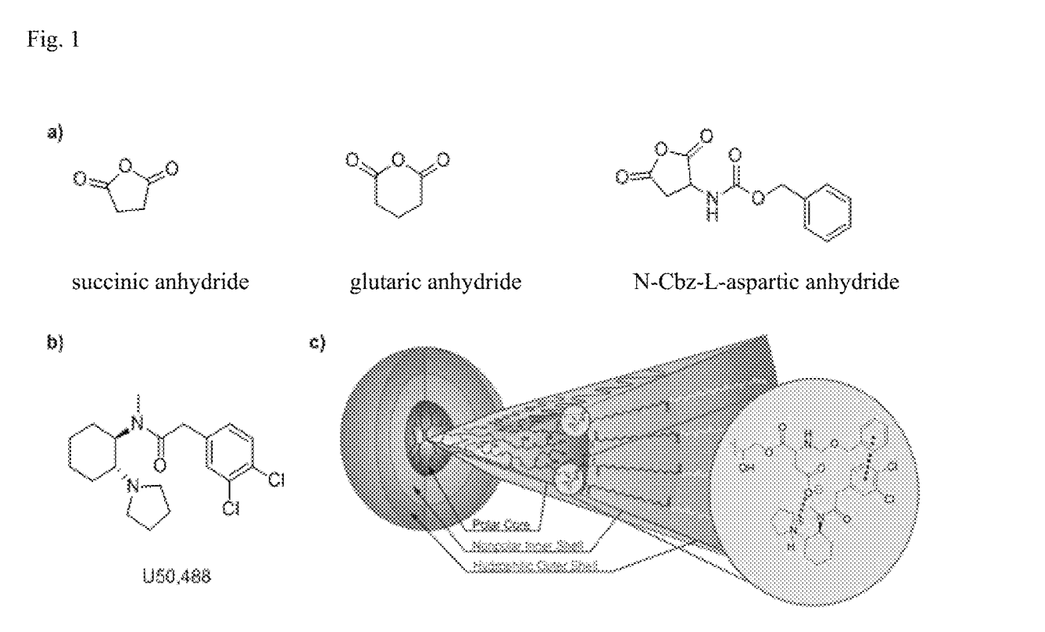
FIG. 1 A Structure of the three selected anchor molecules. B Structure of U50488. C Representation of the N-Cbz-L-aspartic acid-functionalized nanocarrier and the interactions with the active ingredient U50488 (red: salt bridges, blue: π-π interactions).

In one embodiment of the invention, nanocarriers are provided in association with the analgesic which have a novel ionic key-lock mechanism that allows one nanocarrier to encapsulate a variety of drugs. This key-lock principle is realized, for example, by the synthesis of CMS (core multishell) nanocarriers which are equipped at their core with additional anchor molecules, e.g. free acid groups. Succinic and glutaric anhydrides, for example, may be used as possible reactants, since they can undergo a direct reaction with the core of the nanocarriers (FIG. 1a).

Another interesting candidate are derivatizations with peptides or amino acids, e.g. with N-Cbz-L-glutamic anhydride or N-Cbz-L-aspartic anhydride. In addition to the acid group, this protected, cyclized amino acid may allow for π-π interactions through the aromatic residue of the Cbz group. Derivatizations with aspartic acid, glutamic acid, phenylalanine are also possible. As peptides, e.g. peptides can be used which contain 2-10 amino acids, wherein preferably one or more of the recited amino acids is included.

The nanocarrier may be a positively or negatively charged core multi-shell nanocarrier with a hyperbranched dendritic polyglycerol polymer, which is equipped with an amino group-containing compound at the core or via a linker. Such compounds may e.g. be amines, especially primary, secondary, or tertiary amines, and amino acids or derivatives thereof, e.g., alanine or alanine derivatives or glycine or derivatives thereof such as dimethylglycine, N-boc-glycine or tritylglycine. Derivatives are preferably amino acids activated with a linker.

Alternatively, within the scope of the invention, novel nanocarriers can be used which are obtainable by a process in which core multi-shell nanocarriers (FIG. 1c), such as core-ester bond-diacid-ester bond-m-PEG are contacted with acids, bases or other suitable chemical reagents such as enzymes, e.g., an esterase, under suitable conditions and for a suitable time, to partially remove the top shell of the nanocarrier. This leads to a nanocarrier according to the invention comprising multiple negative charges.

Core multi-shell nanocarriers of the type core-amide bond-diacid-ester bond-m-PEG, in which the shell is linked to the dendritic core via an amide bond, can also be partially cleaved under suitable conditions.

If, e.g., the following is used as reactant, 2-10 kDa=hPG-core size
x=Size of the inner shell with e.g. x=13 for the $C_{15}$-diacid
y=mPEG size e.g. 350 for mPEG350 with a Mn of 350 g/mol or e.g. 6 for the number of repeat units
n=degree of functionalization of the core with shell e.g. 70% the nanocarriers prepared in this way can have, e.g., the following structure:

Hydrolysis CMS Based on Pure Ester Basis b=number of free additional OH groups due to complete cleavage of the shell
m=number of new free acid groups, due to partial hydrolysis of the shell Hydrolysis CMS Based on Ester and Amid a=number of free additional amine groups due to complete cleavage of the shell
m=number of new free acid groups, by partial hydrolysis of the shell.

It should be noted that under physiological conditions, amines are positively charged and carboxylic acids are negatively charged, which is not shown in the formulas above for the sake of better readability.

The invention thus also provides a method for producing a multi-shell nanocarrier with positive or negative charge, comprising steps of generating the charge by partial cleavaging of ester bonds or amide bonds, as well as nanocarriers obtainable by the process. This method may be part of a method of making compositions or kits of the invention. In a second step, the prepared nanocarriers may then be non-covalently or covalently loaded or mixed with an analgesic to produce a pharmaceutical composition.

In the context of the invention, the analgesic is preferably an opioid. Advantageously, the analgesic has an agonistic or partial agonistic activity on an opioid receptor selected from the group comprising mu receptor, kappa receptor and delta receptor. The opioid is preferably a kappa receptor agonist such as nalbuphine.

In one embodiment, the opioid is a kappa receptor agonist covalently bound to the nanocarriers, e.g. to the nanocarriers as described in DE 102014008575.9, i.e., a conjugate of a hydrophilic polymer such as polyglycerol with biodegradable anionic end groups such as succinate, which are linked to an analgesic agent such as morphine or another opioide receptor ligand, e.g., via an ester group.

Opioids useful in the invention are, e.g., tramadol, tilidine, pethidine, codeine, piritramide, morphine, levomethadone, fentanyl, alfentanil, remifentanil, sufentanil, pentazocine, butorphanol, nalbuphine, buprenorphine, methadone, U50488 (2-(3,4-dichlorophenyl)-N-methyl-N-[(1R,2R)-2-pyrrolidin-1-ylcyclohexyl]acetamide), U69593 (2-(3,4-dichlorophenyl)-N-methyl-N-[(1R,2R)-2-pyrrolidin-1-ylcyclohexyl]acetamide), HZ-2 (dimethyl 3,7-dimethyl-9-oxo-2,4-dipyridin-2-yl-3,7-diazabicyclo[3.3.1]nonane-1,5-dicarboxylate), BRL 52537 (2-(3,4-dichlorophenyl)-1-[(2S)-2-(pyrrolidin-1-ylmethyl)piperidin-1-yl]ethanone) and bremazocine and other benzomorphane derivates such as e.g. moxazozine. Preferably, the opioid is U50488, U69593, HZ-2, BRL-52537 or bremazocine, most preferably, it is U50488.

The use of nalbuphine in the invention provides a particularly useful profile of effects and undesirable effects.

The composition according to the invention preferably is a pharmaceutical composition. The kit according to the invention can also be used pharmaceutically and is then referred to as a pharmaceutical composition.

In the context of the medical use according to the invention, it is also possible to use other active agents, instead of analgesic agents, in combination with a nanocarrier according to the invention, for use in the treatment of a disease or disease symptom through the peripheral action of the agent, wherein the effect of the agent in the central nervous system is reduced in comparison to a corresponding composition without nanocarrier. Thus, by the combination with the nanocarrier, the undesirable effects otherwise mediated through the central effects of the agent can be reduced or avoided. The active agents contained in such compositions, when administered without the nanocarrier, have both peripheral action as well as action in the central nervous system. The disease or the disease symptom is treated within the scope of the invention by the peripheral action of the active ingredient. The composition may also be in kit form.

Preferably, the active ingredient in the invention is an analgesic, e.g. an opioid, and pain is treated.

The pharmaceutical composition or the pharmaceutical kit optionally comprise further active agents and/or adjuvants. For example, various opioids, e.g. with a different spectrum of activity at different opioid receptors, or other analgesics and/or anti-inflammatory agents can be comprised. The composition may be formulated in saline (e.g., 0.9% NaCl) or buffer (e.g., phosphate-buffered saline, pH 7.2-7.4). It may be a sustained-release composition, e.g. in combination with hydrogels or lipogels suitable for long-term provision of the active agent.

The pharmaceuticals of the invention may be formulated for administration to a human. Alternatively, they may also be veterinary pharmaceuticals, e.g. formulated for administration to pets such as cats, dogs, horses, rabbits, guinea pigs or hamsters, mice or rats.

The pharmaceutical composition may be formulated for intravenous, intramuscular, intraperitoneal, subcutaneous, pulmonary or dermal administration. Administration is also possible via an implant or a semi-automatic or manual pain pump system. While a local administration is possible, the benefits of the invention, namely, the suppression of the central action of the drug, are more apparent with systemic administration.

In the case of a kit, this may be a self-mixing or premixed two-component syringe.

The pharmaceutical composition or the pharmaceutical kit according to the invention is suitable for use in the treatment of pain and/or inflammation, preferably, in acute or chronic pain. The compositions according to the invention are particularly suitable for the treatment of pain associated with inflammation.

In this, by activating peripheral opioid receptors, pain is reduced, but a penetration of the BBB is reduced in comparison to a corresponding composition (the same concentration of the same active ingredient, without nanocarrier, otherwise with the same excipients, and the same administration form).

The covalent or noncovalent combination of nanocarrier and the analgesic which interacts with the opioid receptor is also referred to as NANO-O within the scope of the invention. It has a high molecular weight and hydrophilicity and has been tailored substantially to release the active agent in acidic, inflamed and/or injured tissue, while preventing or reducing permeation through the BBB. In contrast to conventional opioids, intravenous NANO-O essentially activates peripheral opioid receptors, and thus produces analgesia in painful inflamed tissue, without the occurrence of central side effects such as sedation and respiratory depression or intestinal side effects (constipation). Measured concentrations of the active agent in the brain and in the blood are very low, but it is selectively released in the inflamed tissue and at acidic pH. Thus, NANO-O is a novel macromolecular analgesic drug class that works on peripheral opioid receptors in injured tissues, reducing central or intestinal side effects.

According to the present invention, advantageously, undesirable (central) effects such as addiction, respiratory depression, nausea, sedation, constipation, neonatal depression, hallucinations, and depression-like symptoms induced by activation of opioid receptors in the intestinal or central nervous system are reduced compared to a composition without nanocarrier, or preferably, they do not occur.

This patent application thus describes a new class of drugs which does not aim at the targeted release of active agent via tissue-specific antigens or receptors. By contrast, the inventors make use of the surprising finding that the transfer of analgesics, in particular, opioids, through the BBB, and/or preferably through the blood vessel barrier in the non-inflamed (intact) gastrointestinal tract, as well as through the placental barrier, is blocked by the nanocarriers used according to the invention. They also exploit the characteristics of the most prevalent form of clinical pain, i.e., pain caused by localized or disseminated inflammation.

Inflammations are associated with tissue acidosis caused by the release of protons from damaged cells. Tissue acidosis is thus an essential component of many painful syndromes, such as, e.g., rheumatoid arthritis, osteoarthritis, endometriosis, irritable bowel syndrome, neurogenic migraine, neuropathic pain, cancer, trauma, surgery and wounds [Steen, K. H. et al., Pain 66, 163-170 (1996), Woo, Y. C. et al., Anesthesiology 101, 468-475 (2004); Stein, C. et al., Brain Res Rev 60, 90-113 (2009)]. Chronic inflammatory diseases are currently among the most common health threats worldwide [Tabas, I. et al., Science 339, 166-172 (2013)]. Furthermore, inflamed tissues are characterized by fenestration and more permeable capillaries.

The NANO-O that we found selectively releases the active agent peripherally and, because of the characteristics of the nanocarrier, also preferentially in inflamed tissue, and it produces analgesia by activating peripheral opioid receptors. This effect can occur both via mu, kappa and delta opioid receptors or a mixture thereof.

Due to the insurmountability of the BBB, it is to be expected that if mu-receptor agonists are used as intended, there is no danger of addiction, and the danger of tolerance is reduced due to the peripherally acting mechanism of action.

Linkage of nanocarriers with kappa opioid receptor agonists allows for an easier prescription and better accessibility for patients in human and veterinary applications, as addictiveness is significantly reduced even when used improperly. In particular, an abuse after extraction of the drug substance from the drug product by the patient is excluded, since, in this case, the dysphoric side effect and the aversive side effect successfully prevent any risk of addiction.

Therefore, in order to produce the effect of the present invention, the nanocarrier should be sufficiently soluble in blood and tissue fluids to allow for sufficient transfer of the drug to the inflamed tissue, while sufficiently reducing the passage of the drug through the BBB or intestinal blood vessel barrier, such that the drug's effect is primarily limited to the peripheral injured tissue.

The invention provides a new approach to the development of optimized analgesics. The painkillers currently available often result in harmful side effects [Schumacher, M. A. et al., in Basic and clinical pharmacology (eds. Katzung, B. G., Masters, S. B. & Trevor, A. J.) 531-552 (McGraw-Hill Medical, New York, 2009); Zollner, C. et al., Handb Exp Pharmacol, 31-63 (2007); Lancet 382:769-79, 2013]. In contrast, the use of opioids according to the invention, in which the opioids are combined, e.g. associated, with hydrophilic and preferably positively or negatively charged nanocarriers, offers a new generation of opioids with reduced central or intestinal side effects. In particular, negatively charged nanocarriers play an especially important role, since many opioids carry positive charges. By means of the dosage form according to the invention, a transfer of the opioids via the BBB, placental barrier or intestinal blood vessel barrier can be reduced.

Such selective peripherally acting opioid conjugates can achieve a similar analgesic effect compared to classical opioids, but without penetrating barriers such as blood-brain, intestinal or placental barriers. This would exclude side effects such as sedation, dependence, constipation, respiratory or fetal/neonatal depression [Steen, K. H. et al., Pain 66, 163-170 (1996), Woo, Y. C. et al., Anesthesiology 101, 468-475 (2004), Stein, C. et al., Brain Res Rev 60, 90-113 (2009), Tulamo, R. M., et al. Equine Vet J 21, 325-331 (1989), Guthrie, A. J. et al., J Vet Pharmacol Ther 19, 44-49 (1996), Bunczak-Reeh, M. A. et al., J Endod 24, 822-825 (1998). An analgesic treatment of pregnant women or pregnant animals is therefore also possible with the composition according to the invention.

The invention is further illustrated in the following examples, but is not intended to be limited to the examples. The cited references are incorporated by reference in their entirety into the application.

EXAMPLES

1. Manufacturing of Nanocarriers

As a nanocarrier for the example described below, CMS-amide C18-mPEG350 was used. This can be synthesized as described in the patent EP 1796649. This carrier contains free positively charged amino groups, and it was used in the example with U50488 sulfonate.

As further nanocarriers, those of the CMS Ester C15 mPEG350 type were used. This carrier, because of its amphiphilic properties, is well suited for encapsulating both hydrophilic and hydrophobic opioids. It is well soluble in water and it is polar. It is synthesized from a hyperbranched polyglycerol core (hPG) and a mPEG-dicarboxylic acid monoester. Both syntheses are known from the literature [Sunder, A. H. et al., Macromolecules 32, 4240-4246 (1999); Sunder, A. et al., Chemistry 6, 2499-2506 (2000); Haag, R. et al., J Comb Chem 4, 112-119 (2002); Radowski, M. R. et al., Angew Chem Int Ed Engl 46, 1265-1269 (2007)]. To combine the mPEG-dicarboxylic acid monoester with the hPG core, the core is first reacted with thionyl chloride in dichloromethane to the corresponding acid chloride. Subsequently, the acid chloride is reacted with the hPG in pyridine to form the final nanocarrier. The purification of the nanocarrier takes place by membrane filtration with membranes which have a specific molecular weight exclusion limit. This nanocarrier may additionally be equipped with suitable molecules that interact with the active ingredient used. For this purpose, the hydroxy groups on the hPG are partly pre-reacted with these molecules. As a concrete example, we use succinic anhydride here. The succinic anhydride is dissolved in pyridine with catalytic amounts of dimethylaminopyridine and the hPG, and it is bound to the hPG via a ring-opening reaction. The hPG-succinic acid is then reacted with the mPEG-dicarboxylic acid monoester as described above. Subsequent purification is likewise effected by membrane filtration.

A further possibility of increasing the number of free negatively charged carboxylate groups can be realized by controlled addition of an acid, a base or a suitable enzyme which cleaves some of the ester bonds of this nanocarrier type, and thereby precisely adjusts the desired charge density. At the same time, this reaction creates "pockets" in the nanocarrier that promote enhanced non-covalent drug association. Subsequent neutralization or inactivation of the enzyme terminates this reaction. The product is purified by diafiltration.

Another example of a carrier suitable for encapsulation are nanocarriers of the type CMS ester C15 mPEG 350 with covalently linked peptides and amino acids or their derivatives. The use of suitable amino acids or their derivatives having an ionic and/or aromatic group, e.g. aspartic acid, glycine, N, N-dimethylglycine, glutamic acid, phenylalanine, or also protected amino acids such as e.g. N-Cbz-L-aspartic acid, N-Cbz-L-glutamic acid, renders additional ionic and/or pi-pi interactions with the drug possible. These nanocarriers are synthesized in a sequential, scalable multistage process. The purification of the product takes place e.g. by diafiltration.

2. Preparation of a Composition According to the Invention Comprising Nanocarriers and Opioids (NANO-O) without a Covalent Link CMS Nanocarrier of the type hPG (Mn 10k) (octadecane-dioic mPEG350 ester) amide (degree of functionalization between 55 and 75%) and U50488 sulfonate were dissolved in 0.9% NaCl in a mass ratio of 1:4.

The samples were stirred at 1200 rpm for 22 h. Subsequently, a sterile filtration (200 nm RC) was made. The NANO-O is used in Example 3.

3. Analgesic Effect of a Composition According to the Invention

Figure 2:
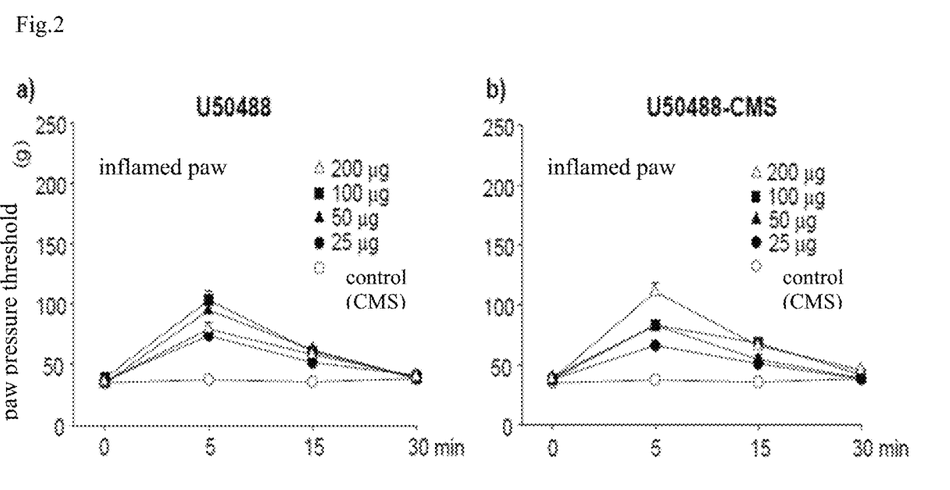
FIG. 2 Analgesic effects of U50488 (a) and U50488 CMS (b) after intraplantar injection into the inflamed paw in rats with unilateral hind paw inflammation (mean±SEM, N=3 rats per group). The doses were calculated as free base.

To detect the analgesia selectively induced in inflamed tissue by NANO-O, local inflammation was induced by intraplantar (i.pl.) injection of complete Freund's adjuvant (CFA) into a hind paw of rats [Stein, C. et al., Pharmacol Biochem Behav 31, 445-451 (1988)]. After four days, the so-called paw pressure threshold (PPT) was measured by means of an algesiometer. The paw pressure threshold indicates the pressure at which the rat feels a painful stimulus and pulls the paw back. In our experiments, initial PPT in inflamed paws was significantly reduced (hyperalgesia), corresponding to results of previous studies [Stein, C. et al., Pharmacol Rev 63, 860-881 (2011); Stein, C. Anesth Analg 76, 182-191 (1993)] (lower PPT in inflamed paws vs. PPT in non-inflamed, contralateral paws.) The effect of different doses (0-200 μg, calculated as free base) of U50488 or NANO-O in the form of U50488-CMS—each injected i.pl into the inflamed paws—was examined. Dose-dependent PPT increase (analgesia) was already detected in inflamed paws 5-15 min after injection of up to 200 μg U50488 (FIG. 2a) or U50488 CMS (FIG. 2b).

Figure 3:
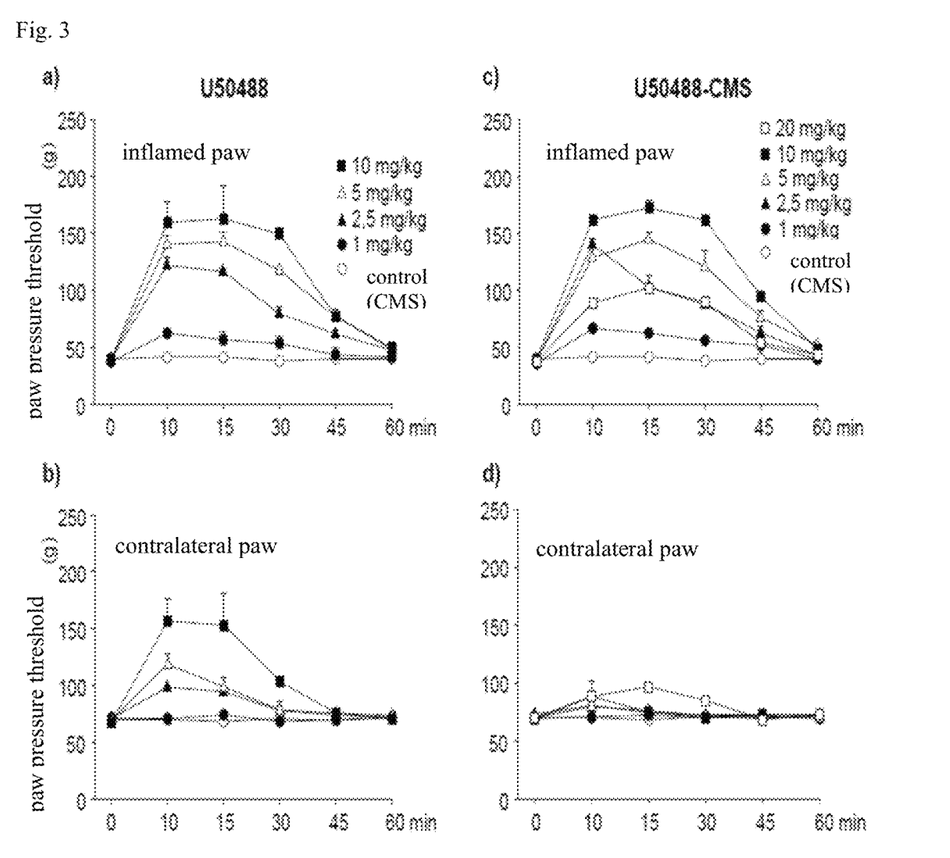
FIG. 3 Analgesic effects of U50488 (a, b) and U50488 CMS (c, d) after intravenous injection in rats with unilateral hind paw inflammation (mean±SEM, N=2-3 rats per group). The doses were calculated as free base.
Figure 4:
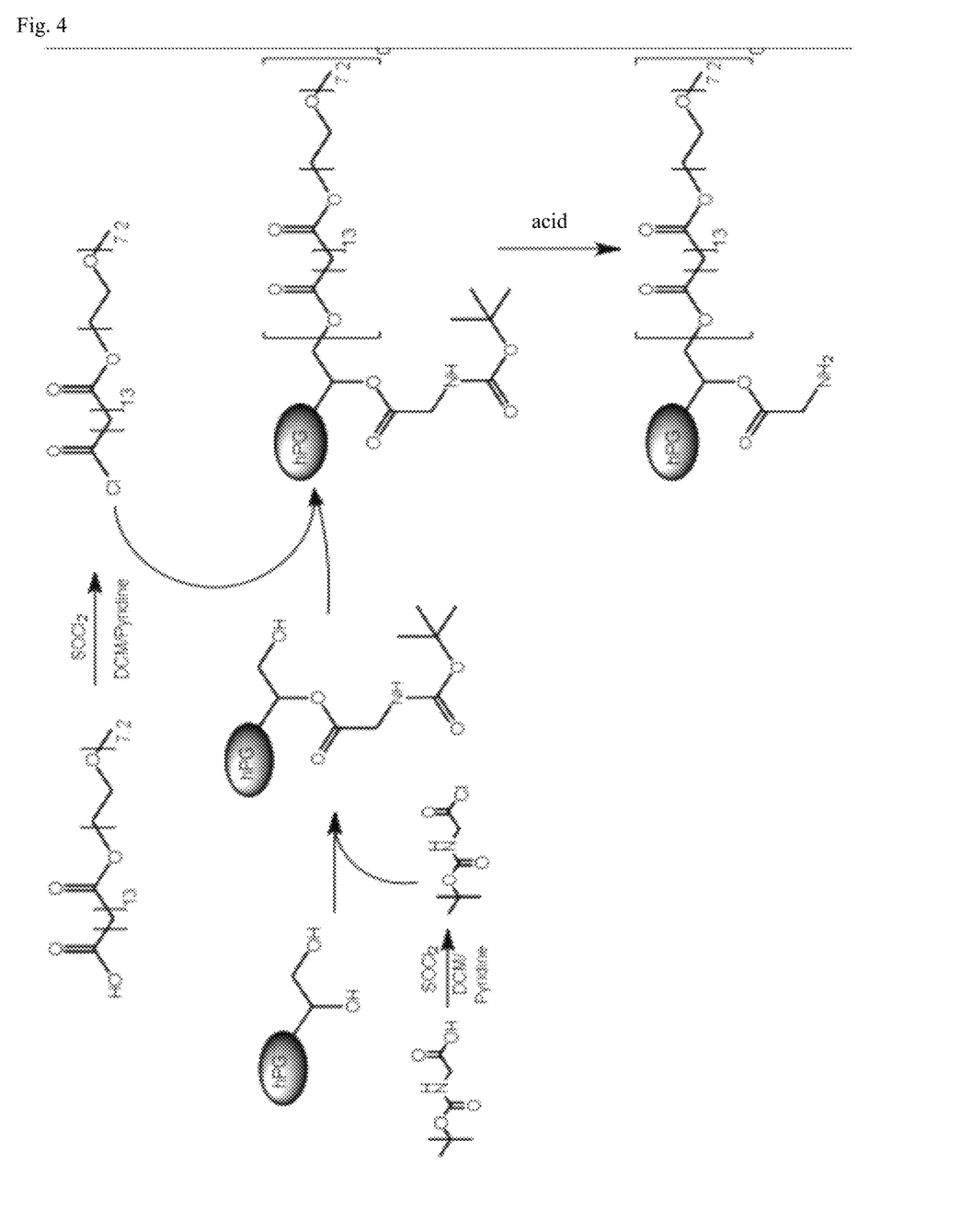
FIG. 4 Exemplary synthesis of a nanocarrier according to the invention
Figure 5:
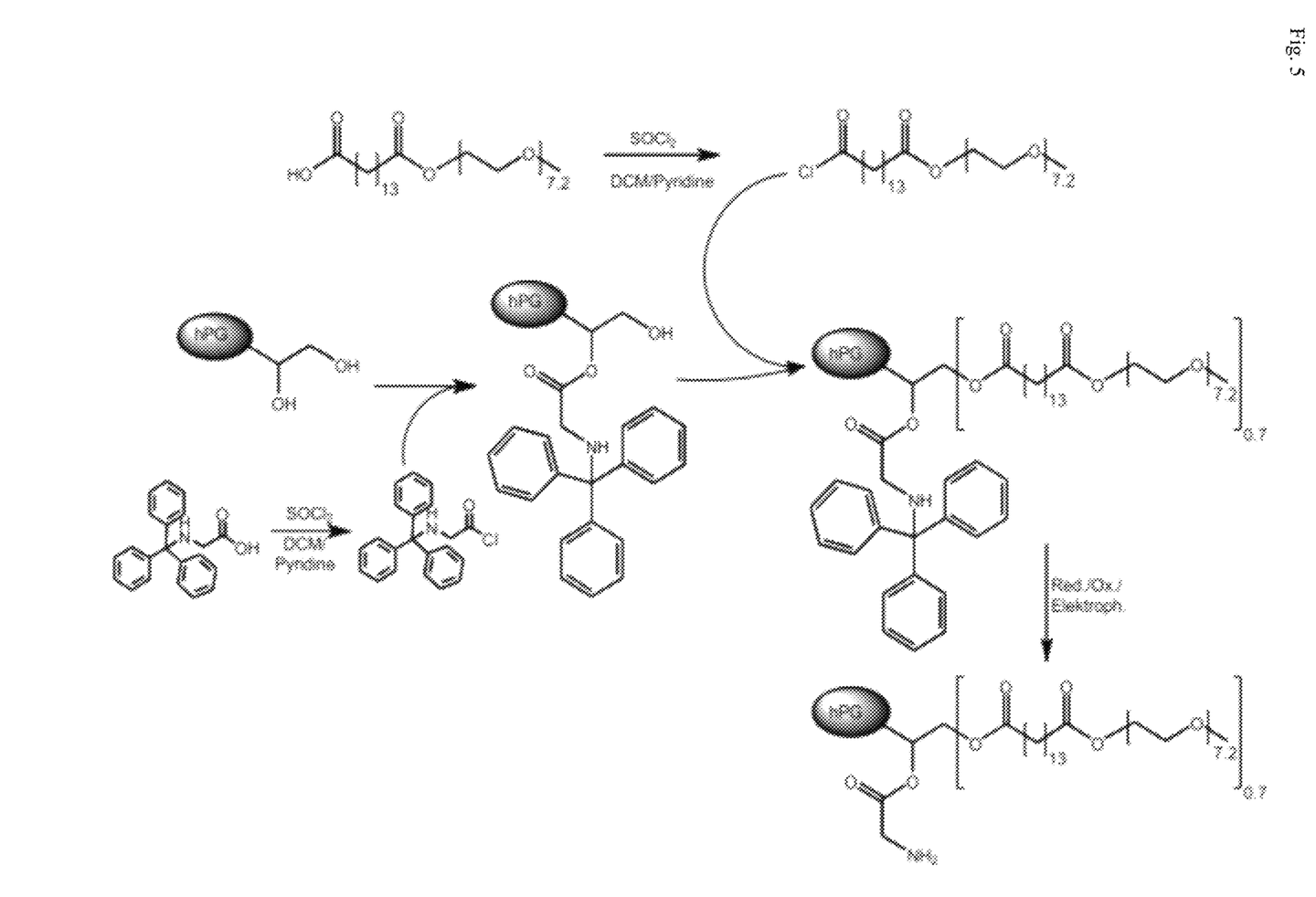
FIG. 5 Exemplary synthesis of a nanocarrier according to the invention

In the following experiments, the change of PPT after intravenous (i.v.) injection of NANO-O was examined. From 10 minutes onward, i.v. administered U50488 caused a dose-dependent analgesic effect in both the inflamed and non-inflamed paws (FIG. 3a, b). Upon application of 10 mg/kg U50488, the upper limit for the PPT (about 160 g) was reached in both paws. A doubling of the dose to 20 mg/kg was not possible for toxicological reasons. In contrast, the i.v. injection of up to 10 mg/kg NANO-O produced an analogous dose-dependent analgesic effect selectively in inflamed, but not in contralateral, non-inflamed paws (FIGS. 3c, d). Upon administration of 20 mg/kg NANO-O, this analgesic effect was reduced due to side effects (FIG. 3c).

After evaluating the analgesic efficacy, it can be summarized that i.v. applied NANO-O exclusively acts on peripheral opioid receptors in the inflamed tissue while i.v. applied U50488 ubiquitously activates both peripheral and central opioid receptors. Interestingly, NANO-O does not cause central analgesic or sedative effects, and has significantly reduced systemic toxicity.

4. Preparation of a Composition According to the Invention, Consisting of Nanocarriers and Opioids (NANO-O) Connected by a Covalent Bond A polymer-drug conjugate having analgesic activity may be obtained via a covalent linkage of the active agent, e.g. an opioid such as nalbuphine, to the hyperbranched polyglycerol, using a glutaric acid group in a two-step manufacturing process.

The hyperbranched polyglycerol, having a molecular weight of 8-9 kDa, corresponding to a degree of polymerization (DPn) of 108-121.5 repeating units (ru), is manufactured using a defined monomer-initiator ratio. Using the equation $DP_n=[M]/[I]$ ([M]: molar amount of monomer, [I]: molar amount of initiator), the required amount of initiator or monomer is calculated. The loading with glutaric acid groups is carried out by an in situ functionalization of hyperbranched polyglycerol with glutaric anhydride. The product is purified, e.g., by diafiltration. The hyperbranched polyglycerol glutarate obtained is reacted with the active agent, e.g., nalbuphine, and again purified, e.g., by diafiltration.

The invention claimed is:

1. A method for selectively delivering an active agent to peripheral tissue of a patient, comprising administering to the patient a pharmaceutical composition comprising
   a hydrophilic nanocarrier comprising a hyperbranched polymer selected from the group consisting of dendritic polymers and dendrimers forming a dendritic core, and
   the active agent which when administered without the nanocarrier has both peripheral action and action in the central nervous system,
   wherein the pharmaceutical composition acts through the peripheral action of the active agent,
   wherein the effect of the active agent is reduced in the central nervous system in comparison to a corresponding composition without nanocarrier,
   wherein the hyperbranched polymer has a degree of branching of at least 25%,
   wherein the dendritic core comprises polyglycerol and has a molecular weight of 5-10 kDa, and
   wherein there is no targeted release of the active agent via tissue-specific antigen or receptors.

2. The method of claim 1, wherein the method is for treating a disease or disease symptom comprising acute or chronic pain or inflammation, wherein the active ingredient is an analgesic.

3. The method of claim 2, wherein the active agent is an opioid, and wherein pain is reduced through activation of peripheral opioid receptors, and wherein the penetration of the blood-brain barrier is reduced in comparison to a corresponding composition without nanocarrier.

4. The method of claim 3, wherein adverse effects elicited by activation of opioid receptors in the central nervous system selected from the group of addiction, respiratory depression, nausea, sedation, constipation, neonatal depression, hallucinations, and depression-like symptoms, are reduced in comparison to a corresponding composition without nanocarrier.

5. The method of claim 1, wherein the composition is administered by intravenous, intramuscular, intraperitoneal, subcutaneous, pulmonary or dermal administration.

6. The method of claim 1, wherein the nanocarrier has negative or positive charges.

7. The method of claim 1, wherein the analgesic and the nanocarrier are covalently linked with each other.

8. The method of claim 1, wherein the analgesic is an opioid selected from the group consisting of nalbuphine, tramadol, pethidine, codeine, piritramide, morphine, levomethadone, fentanyl, alfentanil, remifentanil, sufentanil, pentazocine, butorphanol, buprenorphine, methadone, U50488, U69593, HZ-2, BRL-52537 and bremazocine.

9. The method of claim 1, wherein the nanocarrier is a hyperbranched dendritic polyglycerol polymer selected from the group consisting of core-shell nanocarriers and core-multi-shell nanocarriers.

10. The method of claim 2, wherein the analgesic is an opioid having an agonistic or partial agonistic activity on a kappa opioid receptor.

11. The method of claim 2, wherein the method is for treatment of pain associated with inflammation.

12. The method of claim 3, wherein adverse effects elicited by activation of opioid receptors in the central nervous system selected from the group of addiction, respiratory depression, nausea, sedation, constipation, neonatal depression, hallucinations, and depression-like symptoms do not occur.

13. The method of claim 1, wherein the analgesic is an opioid having an agonist or partial agonist activity on an opioid receptor selected from the group consisting of kappa receptor, mu receptor and delta receptor.

14. The method of claim 9, wherein the nanocarrier consists of a dendritic core and of at least two shells, an inner shell having a first linker connected to the dendritic core and an outer shell having a second linker connected to the inner shell.

15. A method for treating a disease or disease symptom comprising acute or chronic pain or inflammation in a subject in need thereof, comprising administering to the patient a pharmaceutical composition comprising
   a hydrophilic nanocarrier comprising a hyperbranched polymer selected from the group consisting of dendritic polymers and dendrimers forming a dendritic core, and
   an active agent which when administered without nanocarrier has both peripheral action and action in the central nervous system,
   wherein the pharmaceutical composition acts through the peripheral action of the active agent,
   wherein the effect of the active agent is reduced in the central nervous system in comparison to a corresponding composition without nanocarrier, and
   wherein the hyperbranched polymer has a degree of branching of at least 25%,
   wherein the dendritic core comprises polyglycerol and has a molecular weight of 5-10 kDa,
   wherein the active ingredient is an analgesic, and
   wherein the transfer of analgesics through the blood-brain-barrier is blocked by the nanocarriers.

* * * * *